US010098564B2

(12) United States Patent
Sela et al.

(10) Patent No.: US 10,098,564 B2
(45) Date of Patent: Oct. 16, 2018

(54) METHOD, SYSTEM AND APPARATUS FOR TRACKING CORTICAL STIMULATOR LOCATIONS

(71) Applicants: Gal Sela, Toronto (CA); Sean Jy-shyang Chen, Toronto (CA)

(72) Inventors: Gal Sela, Toronto (CA); Sean Jy-shyang Chen, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/107,280

(22) PCT Filed: Aug. 21, 2015

(86) PCT No.: PCT/IB2015/056351
§ 371 (c)(1),
(2) Date: Jun. 22, 2016

(87) PCT Pub. No.: WO2017/033040
PCT Pub. Date: Mar. 2, 2017

(65) Prior Publication Data
US 2017/0188880 A1 Jul. 6, 2017

(51) Int. Cl.
*A61B 5/06* (2006.01)
*A61B 6/12* (2006.01)
*A61B 6/00* (2006.01)

(52) U.S. Cl.
CPC ............... *A61B 5/06* (2013.01); *A61B 6/12* (2013.01); *A61B 6/501* (2013.01); *A61B 6/5247* (2013.01)

(58) Field of Classification Search
CPC ......... A61B 5/06; A61B 6/501; A61B 6/5247; A61B 6/12

(Continued)

(56) References Cited

U.S. PATENT DOCUMENTS 8,979,871 B2   3/2015  Tyc et al.
2006/0149119 A1*  7/2006  Wang ................. A61N 1/36025
                                                         600/9

(Continued)

FOREIGN PATENT DOCUMENTS

CA   2887799 A1   11/2005
CA   2812959 A1   4/2012

OTHER PUBLICATIONS

International Search Report dated May 13, 2016 issued from the Canadian Intellectual Property Office relating to corresponding PCT International Application No. PCT/IB2015/056351.

(Continued)

*Primary Examiner* — Sanjay Cattungal
(74) *Attorney, Agent, or Firm* — Perry + Currier

(57) ABSTRACT

A method comprises: storing, in a memory of a computing device, (i) a preoperative image of patient tissue obtained using a first imaging modality and registered to a first frame of reference, and (ii) anatomical data defining a plurality of neural tracts in the patient tissue; receiving, at a processor connected with the memory, a location in the first frame of reference for application of a cortical stimulator pad to the patient tissue; receiving, at the processor, a range of influence of the cortical stimulator pad; based on the location and the range of influence, selecting, at the processor, an intersected neural tract from the plurality of neural tracts, a portion of the intersected neural tract being located within the range of influence; and controlling, at the processor, the display to render the preoperative image, the location and the intersected neural tract according to the first frame of reference.

6 Claims, 7 Drawing Sheets

(58) Field of Classification Search
USPC .................................................. 600/407–480
See application file for complete search history.

(56) References Cited

U.S. PATENT DOCUMENTS

2012/0265261 A1* 10/2012 Bikson ............... A61N 1/36025
607/2
2013/0030277 A1* 1/2013 Fahey .................. A61B 5/0492
600/384
2013/0079659 A1* 3/2013 Akhadov ............. A61B 5/0476
600/544

OTHER PUBLICATIONS

Written Opinion dated May 13, 2016 issued from the Canadian Intellectual Property Office relating to corresponding PCT International Application No. PCT/IB2015/056351.

* cited by examiner

METHOD, SYSTEM AND APPARATUS FOR TRACKING CORTICAL STIMULATOR LOCATIONS

FIELD

The specification relates generally to medical imaging, and specifically to a method, system and apparatus for tracking cortical stimulator locations.

BACKGROUND

Neurosurgical procedures, such as procedures operating on the brain, may involve the placement of cortical stimulator electrodes against the outer surface of the brain to monitor electrical activity or apply electrical pulses to the brain. The cortical stimulators are generally placed against the outer surface of the brain, at locations selected manually, based on the surgeon's recognition of gross anatomical features of the brain surface (e.g. the locations of sulci and gyri). As a result, it may be unclear which electrical activity is being measured or stimulated by the cortical stimulators.

SUMMARY

According to an aspect of the specification, a method is provided, comprising: storing, in a memory of a computing device, (i) a preoperative image of patient tissue obtained using a first imaging modality and registered to a first frame of reference, and (ii) anatomical data defining a plurality of neural tracts in the patient tissue; receiving, at a processor connected with the memory, a location in the first frame of reference for application of a cortical stimulator pad to the patient tissue; receiving, at the processor, a range of influence of the cortical stimulator pad; based on the location and the range of influence, selecting, at the processor, an intersected neural tract from the plurality of neural tracts, a portion of the intersected neural tract being located within the range of influence; and controlling, at the processor, the display to render the preoperative image, the location and the intersected neural tract according to the first frame of reference.

According to another aspect of the specification, a tracking marker is provided, comprising a first component detectable under a first imaging modality; a second component detectable under a second imaging modality; and a mounting element connected to at least one of the first component and the second component for mounting the tracking marker on a patient tissue.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
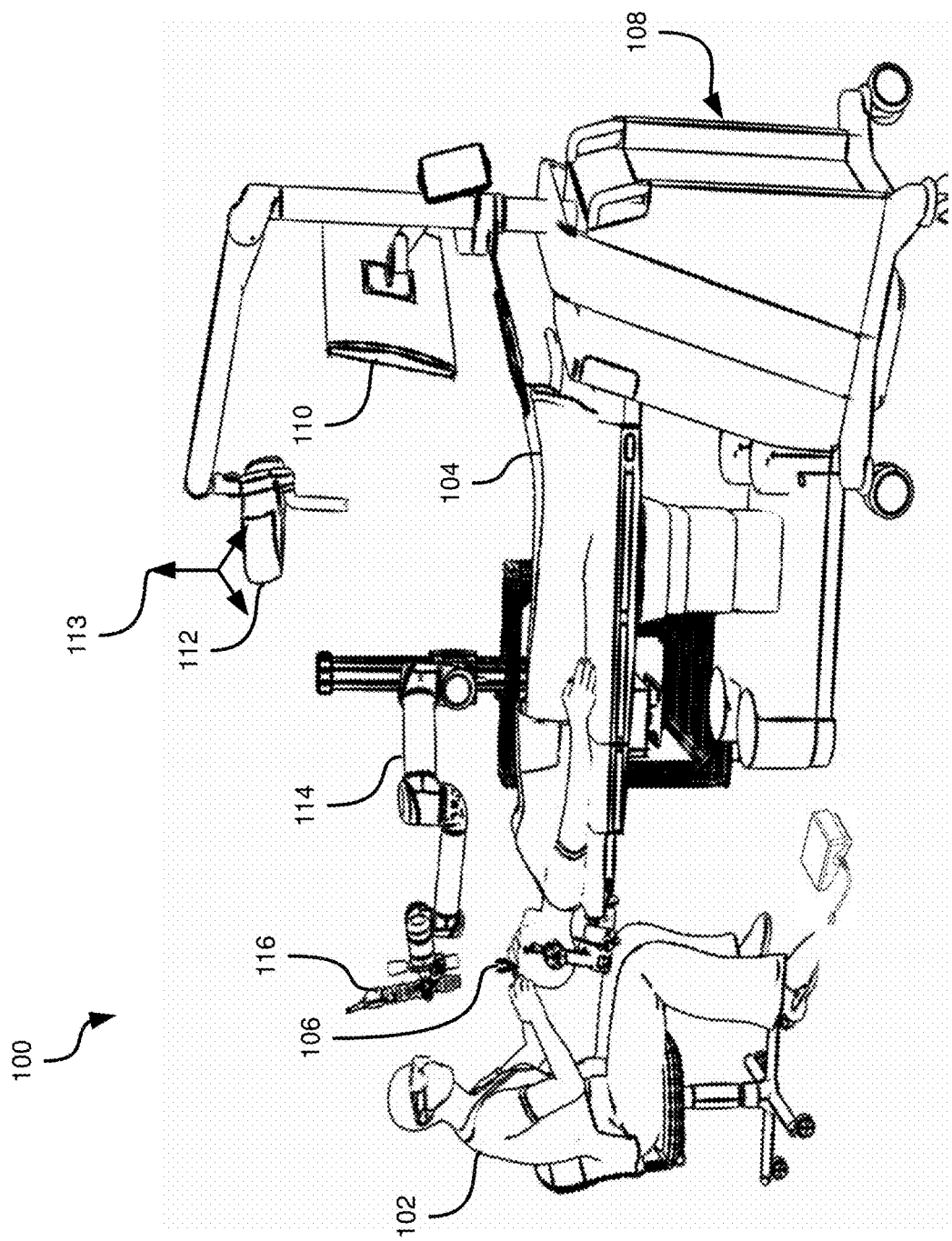
FIG. 1 depicts an operating theatre, according to a non-limiting embodiment.

FIG. 1 depicts a surgical operating theatre 100 in which a healthcare worker 102 (e.g. a surgeon) operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. The description below makes reference to the brain of patient 104 as an example of tissue to which the techniques herein may be applied. It will be understood, however, that those techniques may also be applied to a wide variety of other tissues, including other portions of the cerebrospinal system as well as any other suitable tissue. Thus, when the brain of patient 104 is mentioned below, it is simply an example of the various tissues in connection with which the systems and methods herein may be implemented. Further, the systems and methods described herein need not be restricted to use in minimally invasive surgery, but can also be employed in conjunction with other surgical techniques, including neurosurgical procedures in which a larger portion of the skull is removed to expose the brain.

For minimally invasive procedures, the opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the sulcal folds of the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like. Additional instruments may be employed to conduct the procedure that do not extend into access port 106, such as laser ablation devices (which can emit laser light into access port 106).

Also shown in FIG. 1 is an equipment tower 108 supporting a computing device (not shown) such as a desktop computer, as well as one or more displays 110 connected to the computing device for displaying images provided by the computing device.

Equipment tower 108 also supports a tracking system 112. Tracking system 112 is generally configured to track the positions of one or more reflective markers (not shown) mounted on access port 102, any of the above-mentioned surgical tools and instruments, or any combination thereof. Such markers, also referred to as tracking markers, may also be mounted on patient 104, for example at various points on the head of patient 104. Tracking system 112 may therefore include a camera (e.g. a stereo camera) and a computing device (either the same computing device as mentioned above or a separate computing device) configured to locate the tracking markers in the images captured by the camera, and determine the spatial positions of those markers within the operating theatre. The spatial positions may be provided by tracking system 112 to the computing device in equipment tower 108 for subsequent use. The positions determined by tracking system 112 may be provided in a frame of reference 113 (that is, a coordinate system) centered at a point of origin within the operating room.

The nature of the markers and the camera are not particularly limited. For example, the camera may be sensitive to infrared (IR) or near-infrared (NIR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. The predefined locations, as well as the geometry of each tracked object, are configured within tracking system 112, and thus tracking system 112 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 102 by robotic arm 114, and may capture images of the brain of patient 104 for presentation on display 110. The movement of robotic arm 114 to place external scope 116 correctly over access port 102 may be guided by tracking system 112 and the computing device in equipment tower 108. In other words, one or both of robotic arm 114 and scope 116 bear markers that are detectable by tracking system 112. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images may be collected of patient 104, or at least of the brain or other tissues of patient 104. Such preoperative images may be collected using any of a variety of imaging modalities, including Magnetic Resonance Imaging (MRI). During the procedure, additional images (referred to as intraoperative images) may be collected of the brain or other tissues of patient 104, using any of the above-mentioned additional imaging devices.

In some procedures (generally those performed by removing a section of the skull of patient 104, rather than those conducted through access port 106), cortical stimulator pads are employed. Cortical stimulators generally include adhesive pads embedded with electrical contacts. The electrical contacts, in turn, are connected (e.g. via wires) to hardware (e.g. the above-mentioned computing device, a peripheral of the computing device, or the like) capable of both measuring electrical signals from the electrical contacts (cortical mapping) and applying electrical signals to the contacts (cortical stimulation). In use, cortical stimulators are placed against the outer surface of the brain of patient 104, and are maintained in their placed locations by the adhesive pads. The electrical contacts are thus placed and maintained in contact with the cerebral cortex and can be employed to measure neural activity in the cortex surrounding the contacts, or to apply electrical impulses to the cortex, or both.

The computing device mentioned above is configured, as will be discussed in greater detail below, to track and store the location of cortical stimulators applied to the brain of patient 104, and to automatically retrieve and present various information based on the tracked location of cortical stimulators.

Figure 2:
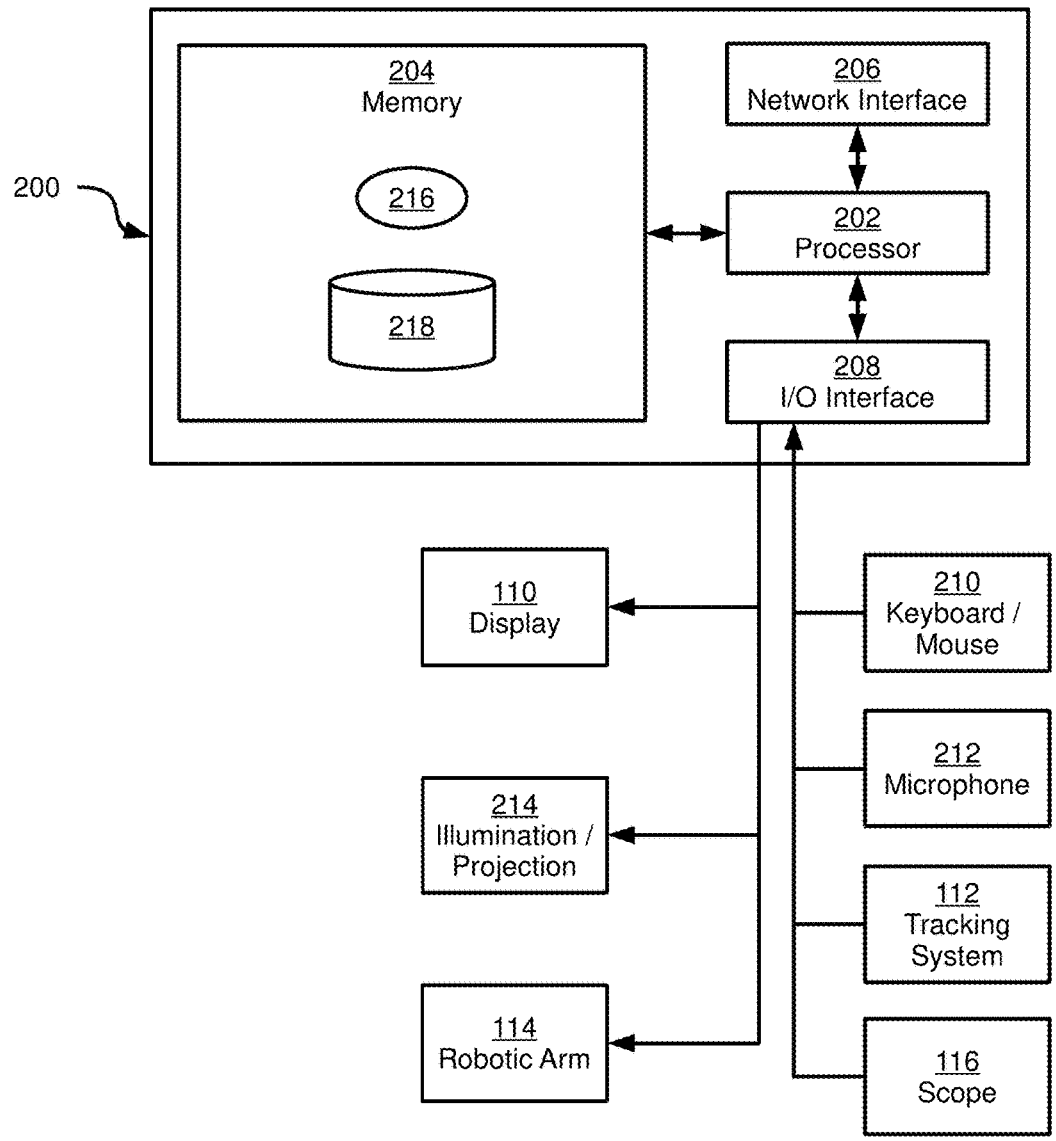
FIG. 2 depicts a computing device of the operating theatre of FIG. 1, according to a non-limiting embodiment.

Before a discussion of the above-mentioned functionality of the computing device, a description of the components of the computing device will be provided. Referring to FIG. 2, a computing device 200 is depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 also includes a network interface 206 interconnected with processor 202. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 also includes an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to input devices including a keyboard and mouse 210, a microphone 212, as well as scope 116 and tracking system 112, mentioned above. Similarly, computing device 200 can be connected to the additional imaging devices mentioned above via interface 208. Also via interface 208, computing device 200 is connected to output devices including illumination or projection components 214 (e.g. lights, projectors and the like), as well as display 110 and robotic arm 114 mentioned above. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 200 via network interface 206.

Computing device 200 stores, in memory 204, a tracking application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, as will be discussed below. Processor 202, or computing device 200 more generally, is therefore said to be "configured" or "operating" to perform those functions via the execution of application 216.

Also stored in memory 204 are various data repositories, including a patient data repository 218. Patient data repository 218 can contain a surgical plan defining the various steps of the minimally invasive surgical procedure to be conducted on patient 104, as well as image data relating to patient 104, such as images captured using modalities such as MRI, and the like.

As mentioned above, computing device 200 is configured, via the execution of application 216 by processor 202, to track and store the locations of cortical stimulators, and to retrieve and present data on display 110 based on the tracked locations. Those functions will be described in further detail below.

Figure 3:
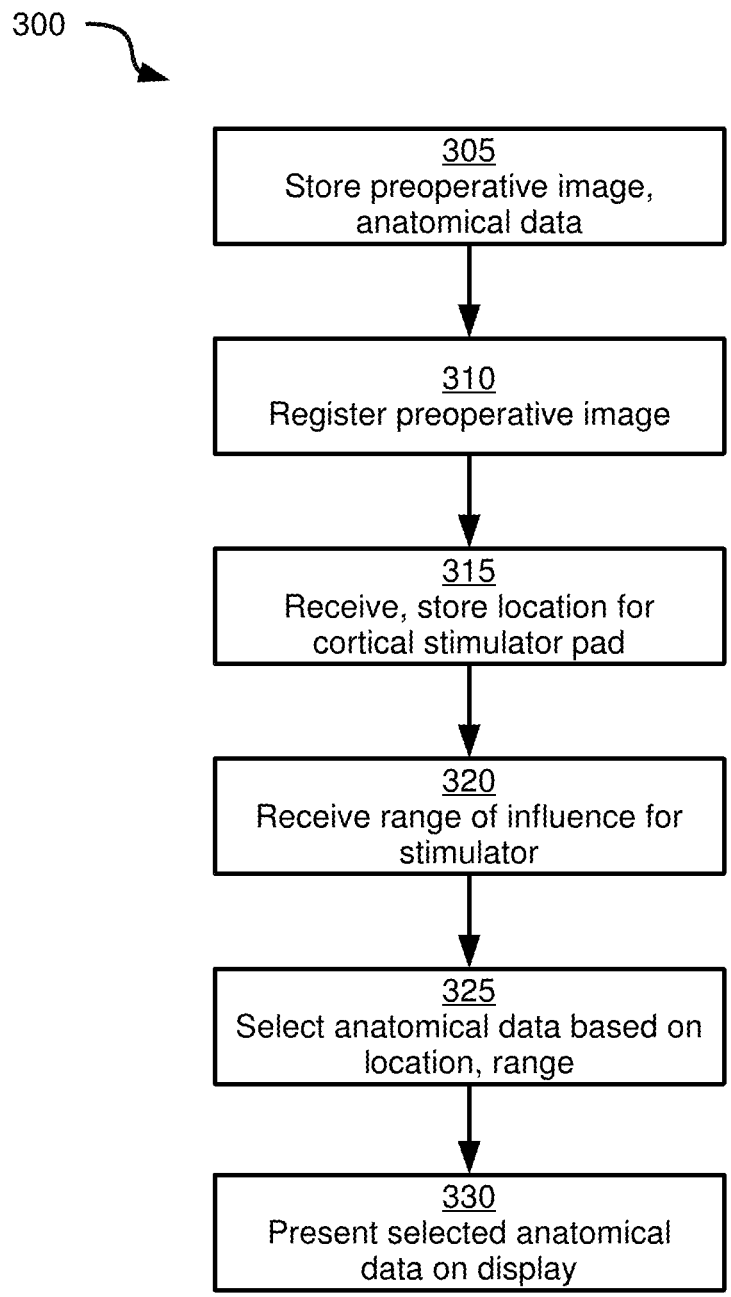
FIG. 3 depicts a method of tracking cortical stimulator locations, according to a non-limiting embodiment.

Referring now to FIG. 3, a method 300 of tracking cortical stimulator locations is shown. The performance of method 300 will be described below in conjunction with its performance within operating theatre 100, and in particular by computing device 200, though it is contemplated that method 300 can also be performed on any other suitable computing device.

Figure 4:
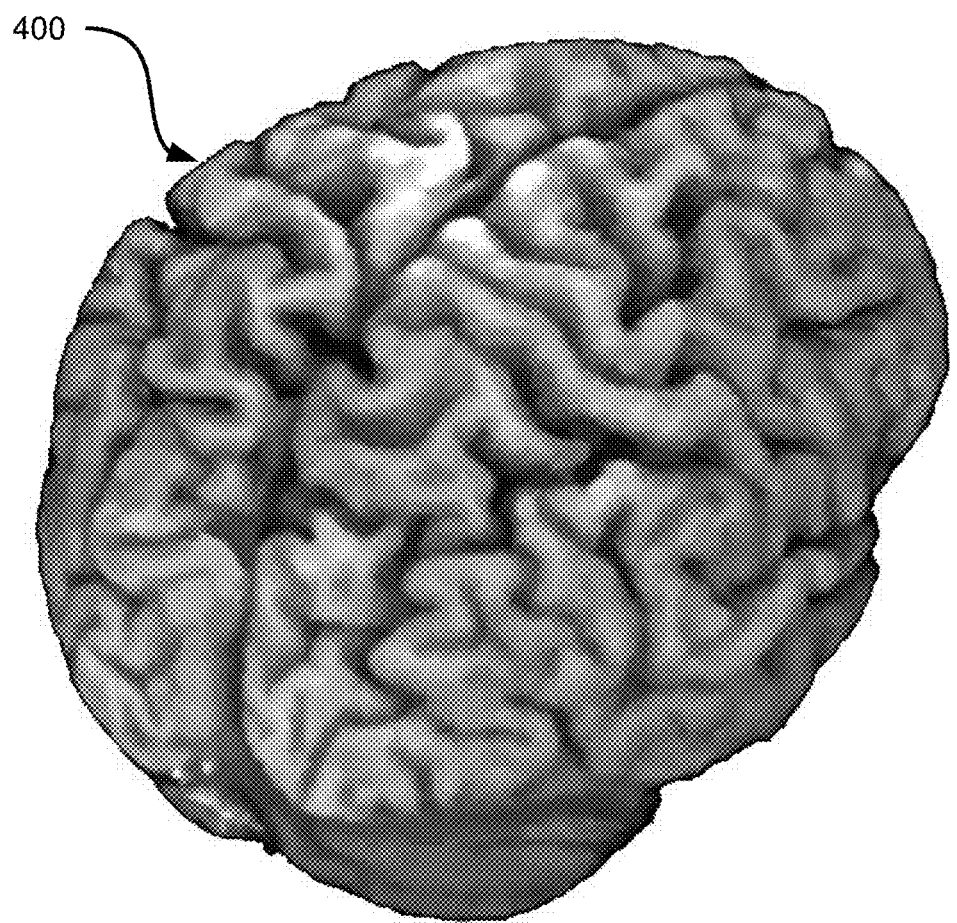
FIG. 4 depicts a preoperative image employed in the method of FIG. 3, according to a non-limiting embodiment.

At block 305, computing device 200 is configured to store a preoperative image of the brain of patient 104, and anatomical data. The preoperative image can be, for example, an MRI image of the brain of patient 104. The preoperative image can be obtained using a variety of imaging modalities other than MRI, however (including, for example, CT). An example preoperative image 400 is depicted in FIG. 4. As seen in FIG. 4, image 400 depicts at least an outer surface of the brain. Image 400 can also include image data depicting various internal structures of the brain, as well as structures surrounding the brain (such as the skull of patient 104, not shown in FIG. 4). Preoperative image 400 can be stored in memory 204 (e.g. in patient data repository 218).

Figure 5:
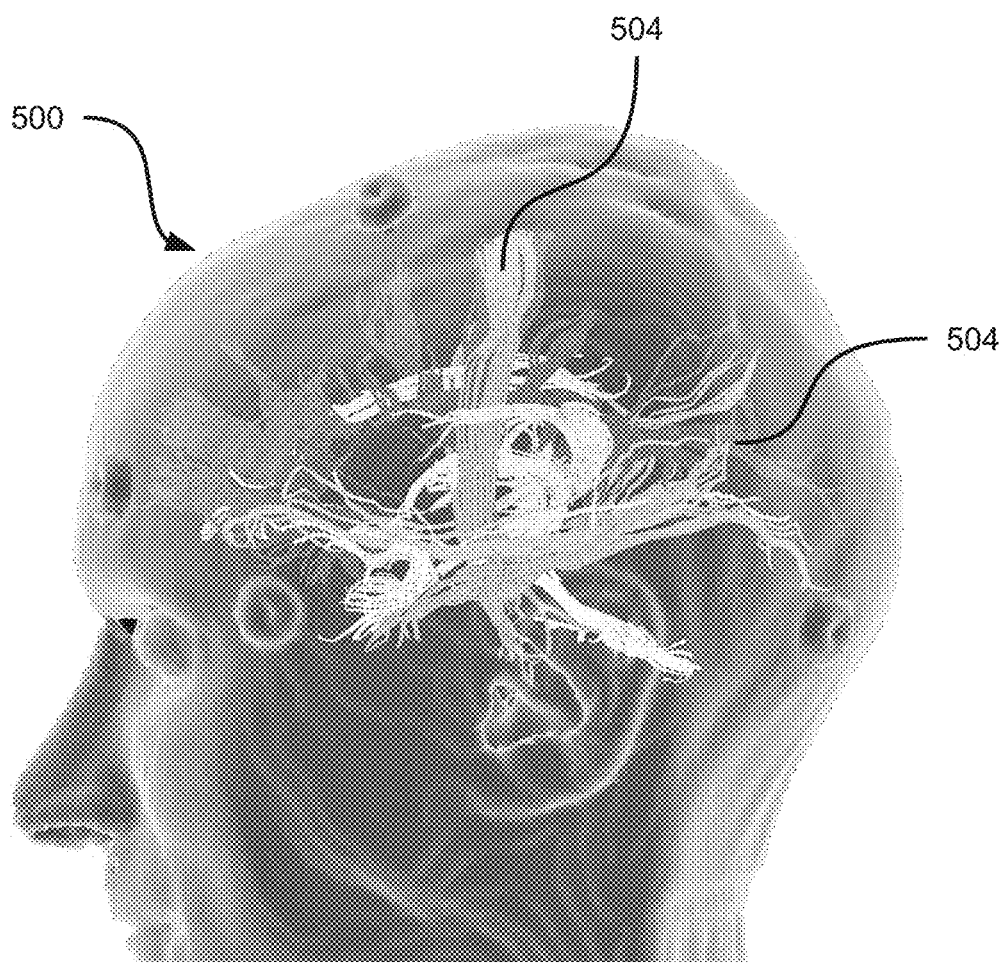
FIG. 5 depicts anatomical data employed in the method of FIG. 3, according to a non-limiting embodiment.

The anatomical data stored in memory at block 305 can also be stored in patient data repository 218. In other embodiments, however, the anatomical data need not be patient-specific, but can instead include atlas data collected from a plurality of patients. The anatomical data can include a wide variety of types of information. In the present embodiment, the anatomical data includes data defining the positions of a plurality of neural tracts within the brain (either the specific brain of patient 104, or a generic brain representative of the brain of patient 104). An example of anatomical data is shown in FIG. 5. In particular, an image 500 of the head of patient 104 is shown (obtained via MRI scanning, for example). Image 500 defines the positions of anatomical features including neural tracts 504 within the brain of patient 104. Tracts 504 represent bundles of tissue connecting portions of the brain. Tracts 504 can be imaged in a variety of ways, including, for example, by diffusion tensor imaging (which employs MRI scanning).

Returning to FIG. 3, at block 310 processor 202 is configured to register preoperative image 400 to frame of reference 113 (that is, to assign coordinates within frame of reference 113 to each pixel, or voxel, in image 400 in place of the image-specific coordinates initially contained in image 400). Various methods of registration may be employed at block 310. For example, a tracked pointer or other instrument (that is, an instrument bearing markers detectable by tracking system 112) can be manipulated by an operator such as healthcare worker 102 to point at physical locations on patient 104 that correspond to previously selected locations within image 400. Having received the location of the pointer within frame of reference 113 from tracking system 112, as well as the previously selected locations in image 400, computing device 200 can be configured to register image 400 with frame of reference 113. Other methods of registering image 400 with frame of reference 113 are also contemplated; examples of such other methods will be discussed herein.

At block 315, processor 202 is configured to receive and store a location in frame of reference 113 for application of a cortical stimulator pad to the tissue (e.g. the brain) of patient 104. In some embodiments, processor 202 can receive the location from tracking system 112. In other words, the performance of block 315 can be preceded by the application of a tracking marker (e.g. a reflective sphere detectable by tracking system 112) to the cortical stimulator, and the detection of that tracking marker by tracking system 112. In other embodiments, the location received at block 315 can be received from an input device such as keyboard and mouse 210, indicating a planned location for the cortical stimulator rather than an actual detected location. Having received the location, processor 202 is configured to store the location in memory 204 (e.g. in repository 218).

At block 320, processor 202 is configured to receive a range of influence of the cortical stimulator whose location was received at block 315. In some embodiments, memory 204 can store data defining various characteristics of the cortical stimulator, including a range of influence. The range of influence can be defined in memory 204 as one or both of a depth and a radius, indicating, respectively, the depth within patient tissue to which electrical impulses from the stimulator travel, and the radius (from the centre of the stimulator, in a direction substantially parallel to the surface of the patient tissue) within the patient tissue from the center of the stimulator to which the electrical impulses travel. The depth and radius can also indicate the furthest extent within the patient tissue that the stimulator can detect natural electrical activity. In other embodiments, such sensitivity can be represented by separate depth and radius parameters.

The performance of block 320, therefore, can involve retrieving the above-mentioned parameters from memory 204. In some embodiments, memory 204 can store such parameters for a plurality of types of cortical stimulator; processor 202 can therefore be configured to select one of the types at block 320 and retrieve the corresponding data. The type of stimulator can be received at processor 202 at block 315. For example, certain marker types can be reserved for certain types of stimulators, and tracking system 112 can be configured to provide processor 202 with not only a location, but also a type of the detected marker.

In further embodiments, the range of influence received at block 320 can be variable. For example, input data can be received at processor 202 (e.g. from keyboard/mouse 210) specifying a depth, radius or both. In still other embodiments, the range of influence of the cortical stimulator may depend on the voltage supplied to the electrical contacts. Processor 202 can therefore be configured to receive input data defining a voltage or other power level, and to determine the range of influence based on a baseline range of influence and voltage stored in memory 204, and the received voltage (e.g. by scaling the baseline range of influence in accordance with the ratio of the baseline voltage to the received voltage).

At block 325, based on the location received at block 315 and the range of influence data retrieved at block 320, processor 202 can be configured to select a subset of anatomical data from anatomical data 500. In the present example, the selected anatomical data includes one or more intersected neural tracts from the plurality of neural tracts defined in anatomical data 500. The intersected neural tracts selected at block 325 are referred to as intersected because at least a portion of each selected neural tract is located within the range of influence of the cortical stimulator. That is, the cortical stimulator, by virtue of its range of influence and current location, can measure electrical activity or induce electrical activity in the selected neural tract.

The selection of neural tracts or other anatomical data at block 325 can be performed in any suitable manner. In general, anatomical data 500 defines the positions and paths of neural tracts, and thus processor 202 can be configured to determine which neural tracts have paths that intersect the volume defined by the stimulator's range of influence.

Figure 6:
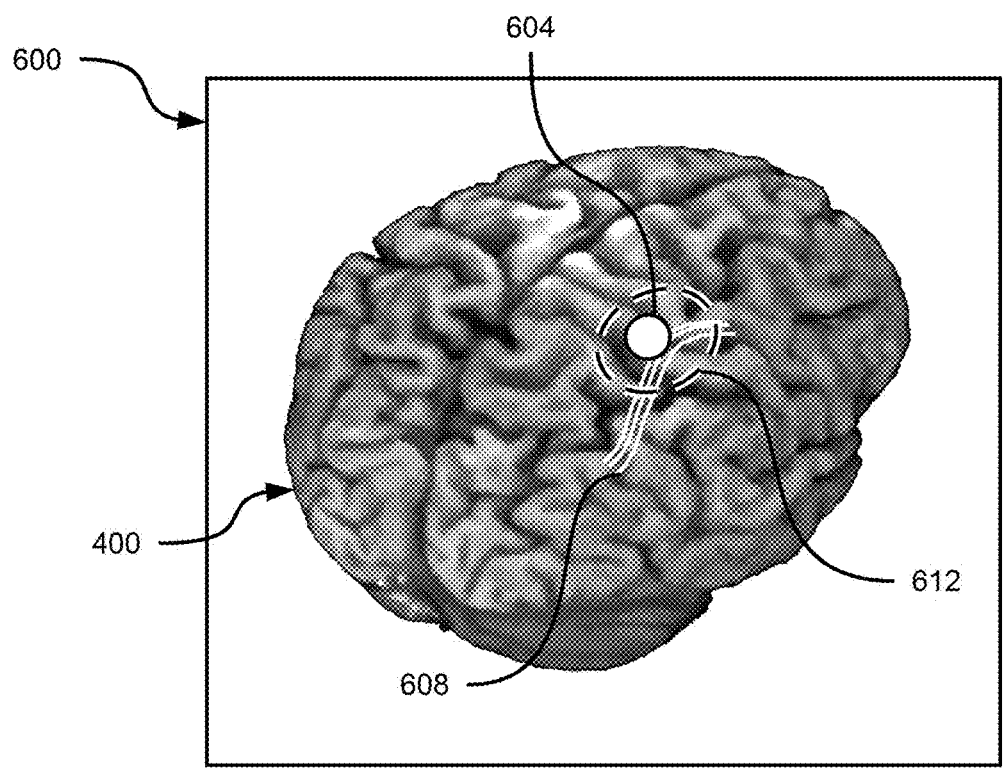
FIG. 6 depicts an interface presented by the computing device of FIG. 2 during the performance of the method of FIG. 3, according to a non-limiting embodiment.

Having selected one or more neural tracts, processor 202 is then configured, at block 330, to present the selected neural tracts on display 110 along with the location received at block 315 and the preoperative image registered at block 310. Turning to FIG. 6, an example interface 600 presented on display 110 is depicted, illustrating a performance of block 330 by processor 202.

Interface 600 includes preoperative image 400 and, overlaid on preoperative image 400, a location marker 604 corresponding to the location received at block 315. In particular, location 604 can indicate the current location, as detected by tracking system 112, of the cortical stimulator. Interface 600 also includes a representation of three neural tracts 608 selected at block 325. As seen in FIG. 6, the paths of neural tracts 608 intersect a range of influence 612 of the cortical stimulator at location 604. Although range of influence 612 is depicted in interface 600, in other embodiments the range of influence can be omitted from display 110.

As will now be apparent to those skilled in the art, the performance of method 300, or portions thereof, can be repeated for a plurality of cortical stimulators or to update the location of any given cortical stimulator in response to relocation of that stimulator (e.g. by healthcare worker 102). Thus, following one or more performances of method 300, memory 204 can store a plurality of cortical stimulator locations received at block 315 and, corresponding to each location, identifiers of one or more neural tracts (identified at block 325) that intersect the range of influence of the stimulator at that location.

Processor 202 can also be configured to generate an interface such as interface 600 in response to receiving a neural tract identifier instead of a cortical stimulator location. For example, processor 202 can be configured to receive (e.g. from keyboard/mouse 210) an identifier of a target neural tract, or identifiers of a plurality of neural tracts. Processor 202 can then be configured to determine, based on the paths of the selected neural tracts as defined in anatomical data 500, a target location on the surface of the brain of patient 104, in frame of reference 113.

The determination of a target location can be performed by, for each selected neural tract, locating the point on the surface of the patient tissue with the smallest distance to the selected neural tract. When a plurality of neural tracts are selected, processor 202 can be configured to select a point on the surface of the patient tissue that minimizes the sum of the distances from that point to each neural tract.

Having selected a target location, processor 202 can be configured to control display 110 to present preoperative image 400, the selected neural tracts, and an indication of the target location, in an interface similar to that illustrated in FIG. 6

As noted above, the tracking of cortical stimulator location can be enabled by the application of markers to the cortical stimulators. In general, any marker that is detectable by tracking system 112 may be employed. In some embodiments, however, it is contemplated that the markers applied to cortical stimulators are multi-modality markers. In general, and as will be discussed below in greater detail, multi-modality markers each include a first component detectable under a first imaging modality, and a second component detectable under a second imaging modality.

Figure 7A:
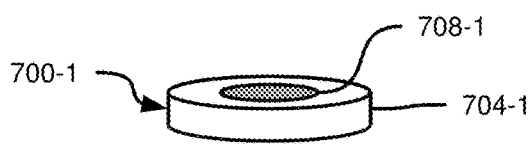
FIGS. 7A, 7B, 7C, 7D and 7E depict example tracking markers for use in the method of FIG. 3, according to a non-limiting embodiment.
Figure 7B:
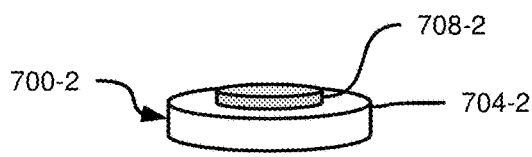
Figure 7C:

Turning now to FIGS. 7A, 7B and 7C, example multi-modality markers 700 (labelled as markers 700-1, 700-2 and 700-3) are illustrated. Each marker 700 includes a first component 704-1, 704-2 and 704-3 (generically referred to as a first component 704) and a second component 708-1, 708-2 and 708-3 (generically referred to as a second component 708). First components 704 are detectable under a first imaging modality, while second components 708 are detectable under a second imaging modality. First components 704, however, are less detectable, or entirely undetectable, under the second imaging modality, and second components 708 are less detectable or undetectable under the first imaging modality.

Markers 700 can also each include a mounting element connected to at least one of the first component 704 and the second component 708. For example, the mounting element can include an adhesive pad on the bottom of the first components 700 (that is, the surface of first components 700 opposite to the second components 708 as illustrated in FIGS. 7A-7C). The mounting element can also include one or more suction cups, or any other suitable structure for attaching the markers 700 to patient tissue.

The imaging modalities referred to above can be any of a variety of modalities. For example, markers 700 as illustrated in FIGS. 7A-7C include first components 704 detectable under MRI imaging, and second components 708 detectable under optical imaging (such as that employed by tracking system 112). Various mechanisms for detecting marker components under optical imaging will now occur to those skilled in the art. The detection of marker components under modalities such as MRI can be performed (e.g. by processor 202) according to any suitable process. For example, processor 202 can retrieve a digital model of the relevant marker 700 and associated patient tissue to be identified. Using the model and other parameters, processor 202 then automatically collects a set of metrics to help extraction of the marker-like features from a subject image (e.g. an MRI scan). The model includes the marker's shape (e.g. a toroidal shape), a slab of tissue that the marker 700 will be located on, the empty space that will be around the marker, as well as a marker coordinate.

Processor 202 can first filter the image using an image-derivative based filter to enhance salient structures. The filtered image is then progressively filtered by processor 202 at different intensity levels using the metrics collected from the model to identify candidate features that may be markers. The model is then aligned and oriented right-side-up with all candidate features and the location of the features in the subject image to determine their similarities and identify features as markers in the image. The coordinates of the markers (e.g. the center of each marker) can be presented on display 110, or via any other suitable output device connected to processor 202.

Other examples of techniques available to the skilled person for detecting marker components under non-optical modalities (e.g. MRI) are discussed in Yin, et al., "An Automatic Registration Method Based on Fiducial Marker for Image Guided Neurosurgery System", *Communications in Computer and Information Science* Volume 402, 2013, pp 114-125. Further examples can be found in Gu, et al., "3D Automatic Fiducial Marker Localization Approach for Frameless Stereotactic Neuro-surgery Navigation", *Lecture Notes in Computer Science* Volume 3150, 2004, pp 329-336; and Tan, et al., "A Template Based Technique for Automatic Detection of Fiducial Markers in 3D Brain Images", *International Journal of Computer Assisted Radiology and Surgery* Volume 1, 2006, pp 47-48.

Thus, first components 704 can include any suitable contrast material that is detectable under magnetic imaging. Such contrast materials can include, for example, a capsule of fluid containing gadolinium, vitamin E, manganese or any other suitable contrast liquid. The capsule can have a variety of shapes and configurations, including a disc shape, a toroidal shape, and the like. Other example first components can include other magnetically active materials, such as iron oxide (e.g. first components 704 can be covered, or partially covered, with paint containing iron oxide).

Second components 708 can include any suitable reflective material that is detectable under optical imaging, such as that performed by tracking system 112. For example, second components can include discs, spheres or the like bearing one or more of a reflective surface, a patterned surface (e.g. a checkerboard pattern, glyph or other suitable pattern) or the like. FIGS. 7A-7C depict three examples of second components 708. Second component 708-1 includes a substantially flat reflective disc centered on one side of first component 704-1. Second component 708-2 includes a raised reflective disc centered on one side of first component 704-2. Second component 708-3 includes a machine-readable graphic, such as a checkerboard pattern. As will be apparent from FIG. 7C, second component 708-3 is not centered on first component 704-3. In other embodiments, second component 708-3 can be centered on first component 704-3. As will now be apparent, second components 708-2 and 708-3 also need not be centered, so long as the position of second components 708 relative to first components 704 is predetermined and fixed. For example, the angular orientation of second component 708-3 can be detected by a camera (e.g. tracking system 112) due to the asymmetrical pattern, and thus when the distance between the center of second component 708-3 and the center of first component 704-3 is predetermined and fixed, the positions of first component 704-3 and second component 708-3 can be related by use of the angular orientation of second component 708-3.

In other embodiments, the first imaging modality can be CT instead of, or in addition to, MRI, and thus first components 704 can include contrast material such as an iodine-containing fluid. For example, first components 704 can contain a fluid that includes both a radio-density enhancing material such as iodine, and a magnetically active material such as iron oxide, to render first components 704 detectable under both CT and MRI. In still other embodiments, markers 700 can include third components detectable by a third imaging modality.

Figure 7D:
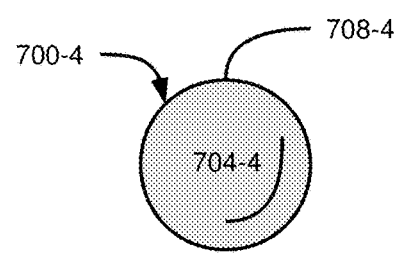
Figure 7E:
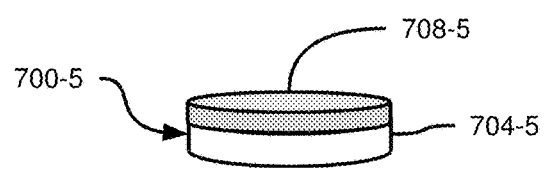

FIGS. 7D and 7E illustrated two additional embodiments of multi-modality markers. For example, FIG. 7D depicts a marker 700-4 including a first component 704-4 in the form of a spherical capsule (e.g. containing MRI-detectable fluid), and a second component 708-4 in the form of a reflective surface on the capsule 704-4 itself. In other words, first component 704-4 is contained within second component 708-4. FIG. 7E, meanwhile, is a variation of marker 700-2 shown in FIG. 7B. In particular, FIG. 7E illustrates a marker 700-5 including a first component 704-5, which can be similar to first component 704-2 described above. Marker 700-5 also includes a second component 708-5, for example in the form of a reflective disc centered on first component 704-5. However, second component 708-5 has a diameter equal to that of first component 704-5. In other embodiments, a variety of other relative sizes of first and second components 704 and 708 are contemplated.

The components of markers 700 can also include physical features such as divots at the center thereof, for guiding a manually-placed pointer instrument tracked by system 112. The toroidal shape mentioned above for the capsules described herein can provide such a divot (at the center of the toroid), allowing detection of the center of the capsule by tracking system 112 via manual placement of the tip of a tracked instrument within the divot. In other embodiments, a divot may be provided on a surface of a non-toroidal marker, such as that shown in FIG. 7E, for example in the form of an indentation centered on a face of second component 708-5. The width and depth of the divot can vary according to the size of the tip of the tracked instrument to be placed within the divot.

It is contemplated that multi-modality markers as described above can be employed to perform block 310 of method 300. For example, multi-modality markers 700 can be placed on patient 104 prior to capturing the preoperative MRI image, and the markers can remain on patient 104 in operating theatre 100 after acquisition of the MRI image. Thus, the first components 704 can be readily detected by processor 202 in preoperative image 400, and the second components 708 can be readily detected (and their locations provided to processor 202) on patient 104. Processor 202 can therefore be configured to register preoperative image 400 to frame of reference 113 based on the predetermined positions of the second components 708 of each marker relative to the first components 704 of each marker.

In further embodiments, multi-modality markers 700 can be applied to cortical stimulators. Thus, second components 708 can be detected by tracking system at block 315. In addition, however, markers 700 can remain on the surface of the brain of patient 104 postoperatively (that is, underneath the skull of patient 104). Although second components 708 can no longer be imaged optically, first components 704 can be imaged via MRI or CT scanning. Processor 202 can therefore be configured to receive a postoperative image and compare the positions of first components 704 detected therein to the locations stored at block 315, for example to determine whether any cortical stimulators have shifted in position. The comparison of marker positions stored at block 315 with marker positions identified in postoperative images can also be employed by processor 202 to register postoperative images with preoperative image 400.

The scope of the claims should not be limited by the embodiments set forth in the above examples, but should be given the broadest interpretation consistent with the description as a whole.

We claim:

1. A method, comprising:
    storing, in a memory of a computing device, (i) a preoperative image of patient tissue obtained using a first imaging modality and registered to a first frame of reference, and (ii) anatomical data defining a plurality of neural tracts in the patient tissue;
    at a processor connected with the memory:
        receiving, from a tracking system connected to the computing device, a location in the first frame of reference of a tracking marker connected to a cortical stimulator pad and detected by the tracking system responsive to application of the cortical stimulator pad to the patient tissue;
        receiving a range of influence of the cortical stimulator pad;
        based on the location and the range of influence, selecting an intersected neural tract from the plurality of neural tracts, a portion of the intersected neural tract being located within the range of influence; and
        controlling a display connected to the processor to render the preoperative image, the location and the intersected neural tract according to the first frame of reference;
    applying the tracking marker to the cortical stimulator pad; the tracking system configured to detect a first component of the tracking marker;
    after applying the tracking marker, obtaining a postoperative image of the patient tissue using a second imaging modality;
    detecting a second component of the tracking marker in the postoperative image; and
    at the processor, registering the postoperative image to the first frame of reference based on the detected second component of the tracking marker.

2. The method of claim 1, further comprising:
    receiving, at the processor, an identifier of a target one of the plurality of neural tracts;
    determining, at the processor, a target location on a surface of the patient tissue for placement of the cortical stimulator to intersect the targeted neural tract with the range of influence; and
    controlling the display to render the target location according to the first frame of reference.

3. The method of claim 1, wherein receiving the range of influence comprises retrieving the range of influence from the memory.

4. A computing device, comprising:
    a memory storing (i) a preoperative image of patient tissue obtained using a first imaging modality and registered to a first frame of reference, and (ii) anatomical data defining a plurality of neural tracts in the patient tissue;
    a display; and
    a processor connected to the memory and the display, the processor configured to:
        receive, from a tracking system connected to the computing device, a location in the first frame of reference of a tracking marker connected to a cortical stimulator pad and detected by the tracking system responsive to application of the cortical stimulator pad to the patient tissue;
        receive a range of influence of the cortical stimulator pad;
        based on the location and the range of influence, select an intersected neural tract from the plurality of neural tracts, a portion of the intersected neural tract being located within the range of influence; and
        control the display to render the preoperative image, the location and the intersected neural tract according to the first frame of reference;
    wherein the tracking marker is applied to the cortical stimulator pad: the tracking system configured to detect a first component of the tracking marker;
    the processor further configured to:
        after application of the tracking marker, obtain a postoperative image of the patient tissue using a second imaging modality;
        detect a second component of the tracking marker in the postoperative image; and
        register the postoperative image to the first frame of reference based on the detected second component of the tracking marker.

5. The computing device of claim 4, wherein the processor is further configured to:
    receive an identifier of a target one of the plurality of neural tracts;
    determine a target location on a surface of the patient tissue for placement of the cortical stimulator to intersect the targeted neural tract with the range of influence; and
    control the display to render the target location according to the first frame of reference.

6. The computing device of claim 4, wherein the range of influence is retrieved from the memory.

* * * * *